United States Patent [19]

Kay et al.

[11] 4,303,597

[45] Dec. 1, 1981

[54] O,O-DIALKYLDITHIOPHOSPHORYL-N-HYDROCARBYLTHIOPHOSPHORAMIDES

[75] Inventors: Edward L. Kay; Delmar F. Lohr, both of Akron, Ohio

[73] Assignee: The Firestone Tire & Rubber Company, Akron, Ohio

[21] Appl. No.: 82,431

[22] Filed: Oct. 5, 1979

[51] Int. Cl.$^3$ ............................................. C07F 9/165
[52] U.S. Cl. .................................. 260/933; 260/783; 525/341
[58] Field of Search ........................................ 260/933

[56] References Cited

U.S. PATENT DOCUMENTS

| | | | |
|---|---|---|---|
| 2,599,341 | 6/1952 | McDermott | 252/46.6 |
| 2,668,836 | 2/1954 | Tolkmith | 260/933 |
| 2,729,667 | 1/1956 | Saul | 260/933 |
| 2,729,668 | 1/1956 | Saul | 260/933 |
| 3,052,596 | 9/1962 | Baker et al. | 260/933 |
| 3,060,080 | 10/1962 | Lorenz et al. | 260/933 |
| 3,155,707 | 11/1964 | Kauer | 260/933 |
| 3,400,106 | 9/1968 | Morita | 260/79.5 |
| 3,419,521 | 12/1968 | Scott et al. | 260/41.5 |
| 3,426,003 | 2/1969 | Leib et al. | 260/79.5 |
| 3,520,808 | 7/1970 | Light | 260/46.6 |
| 3,629,210 | 12/1971 | Apotheker et al. | 260/79.5 |
| 3,635,920 | 1/1972 | Apotheker | 260/79.5 B |
| 3,835,202 | 9/1974 | Elliott et al. | 260/933 |
| 3,867,358 | 2/1975 | Trivette et al. | 260/79.5 C |
| 3,909,447 | 9/1975 | Redmore et al. | 260/933 |
| 3,969,349 | 7/1976 | Trivette et al. | 260/247.1 M |
| 4,017,489 | 4/1977 | Lawrence | 260/243 B |
| 4,065,443 | 12/1977 | Campbell et al. | 260/79.5 B |

*Primary Examiner*—Anton H. Sutto

[57] ABSTRACT

The vulcanization rate of rubber stock compounded for curing is increased by using in the stock for the cure and accelerator of certain O,O-dialkyldithiophosphoryl-N-hydrocarbylthiophosphoramides; the same being, per se, new compositions of matter also useful, inter alia, as lubricating oil additives and for insecticidal purposes.

6 Claims, No Drawings

O,O-DIALKYLDITHIOPHOSPHORYL-N-HYDROCARBYLTHIOPHOSPHORAMIDES

BACKGROUND OF THE INVENTION

There exist many known accelerator agents and systems for the curing and vulcanization of rubber(s) of either the natural or synthetic variety (and mixtures thereof) which are compounded for that purpose. These include various and numerous sulfur-containing materials, as are all set forth in the *VANDERBILT Rubber Handbook*, in Current Edition and which are known for such usage when employed individually or in combination with other materials. The same, needless to mention, also applies to compositions useful as lubricating oil additives, insecticides, and so forth.

Unfortunately, insofar as accelerator materials are concerned, the great preponderance of them tend to be undesirably expensive. As is abundantly evident in the ensuing specification, the novel composition(s) of the present invention, when employed as accelerator ingredients or for any other desired purpose are obtainable and providable by a relatively simply process utilizing generally readily available and relatively low cost starting raw materials.

The prior art in the particular area of present pertainment is of great magnitude. in fact, the basic fundamentals and operational principles and limitations of accelerators and curing agents for the vulcanization or rubber are so well known by those skilled in the art that further elucidation thereof and elaboration thereon is unnecesary for understanding of the advance possibilated by and with the development of the present invention.

The novel compositions of the present invention, useful for the specified and other valuable purposes, are of the general structure and Formula:

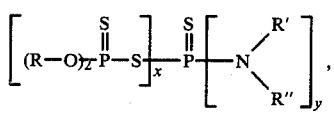

(I)

wherein the integral value (or value as integers) of both x and y is independently as a number from 1 to 2 with the limitation that the numerical sum of x and y in any given instance is 3; and R, R' and R" are independently selected from the group consisting of linear, branch-structured and cyclic aliphatic radicals and/or aromatic radicals and mixtures thereof independently containing from 1 to about 12 carbon atoms and in which group, additionally, R' and R" optionally can be independently and individually a proton (i.e., H+).

Thus, the bonding to the nitrogen atom in the structures of Formula (I) can, in any given instance and as the particular case may be, include either —NH—R'; —N—R'$_2$; or —N—R'—R".

Typically in various embodiments of compounds of the above Formula (I), R, R' and R" can independently be, as selected and desired, methyl, ethyl, n-propyl, isopropyl, n-butyl and its isomers, cyclohexyl, octyl and its isomers (such as 2-ethylhexyl), stearyl, phenyl and so forth.

The prior art does not precisely teach or disclose the novel compositions of the present invention as are defined and delineated by the above Formula (I).

However, some of the prior art of interest includes:

| U.S. PAT. NO. | INVENTOR |
| --- | --- |
| 2,599,341 | McDermott; |
| 2,668,836 | Tolkmith; |
| 2,729,667 | Saul; |
| 2,729,668 | Saul; |
| 3,052,596 | Baker; |
| 3,060,080 | Lorenz; |
| 3,155,707 | Kauer; |
| 3,400,106 | Morita; |
| 3,419,521 | Scott; |
| 3,426,003 | Leib; |
| 3,520,808 | Light; |
| 3,629,210 | Apotheker; |
| 3,635,920 | Apotheker; |
| 3,835,202 | Scotchford; |
| 3,867,358 | Trivette, Jr.; |
| 3,909,447 | Redmore; |
| 3,969,349 | Trivette, Jr.; |
| 4,017,489 | Lawrence; and |
| 4,065,443 | Campbell. |

Of the foregoing prior art, some of the citations do involve some compounds and compositions of remote and non-suggestive relationships to those of Formula (I).

For example, the Campbell Patent (U.S. Pat. No. 4,065,443) discloses accelerators for the vulcanization of rubber having the structure:

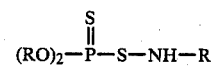

(Noting Col. 3, Lines 60 et seq.).

Similarly, the Apotheker Patents (U.S. Pat. Nos. 3,629,210 and 3,635,920) disclose accelerators having the formulae:

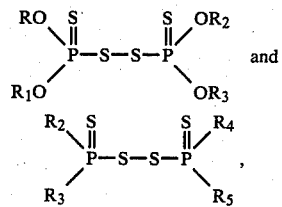

repectively.

Other patents disclosing compounds of structural interest include:

The Tolkmith U.S. Pat. No. 2,668,836, i.e.,

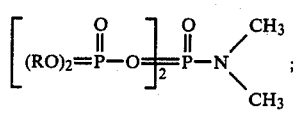

Saul (U.S. Pat. No. 2,729,668), i.e.,

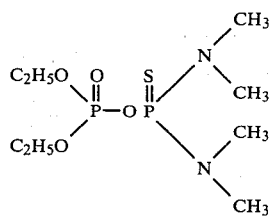

Saul (U.S. Pat. No. 2,729,667), i.e.,

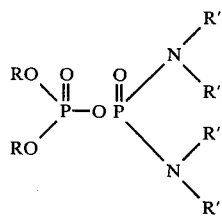

Baker (U.S. Pat. No. 3,052,596), i.e.,

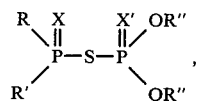

where X and X' is S or O; and
Lorenz (U.S. Pat. No. 3,060,080), i.e.,

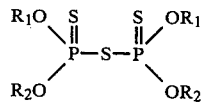

It is of interest to observe that many of the prior art compounds disclosed in the foregoing citations are of primary insecticidal and the like utility.

FIELD AND OBJECTIVES OF THE INVENTION

This invention pertains to the particular and above-delineated O,O-dialkyldithiophosphoryl-N-hydrocarbylthiophosphoramides of the Formula (I) esters of phosphorodithioic acid which, as hereinafter more fully illustrated, can be prepared by a relatively simple process using raw materials that are relatively and in good supply available and not unduly expensive and are capable of use with attendant good results for: (i) the vulcanization of compounded stocks of unsaturated, generally sulfur-vulcanizable natural or synthetic rubber and which provide inherently satisfactory cure rates in and of the rubber being treated and/or fabricated; (ii) as antioxidant additives for mineral lubricating oils; (iii) as insecticides; and so forth—the provision of all of same being amongst the principal aims and objectives of the invention.

SUMMARY OF THE INVENTION

The present invention and the discovery on which it is based relates to novel O,O-dialkyldithiophosphoryl-N-hydrocarbylthiophosphoramides of the Formula (I). The invention also contemplates unsaturated and generally sulfur-vulcanizable natural and synthetic rubber formulations and stocks compounded with and containing the herein-contemplated essential accelerator additament of the invention; plus vulcanized rubber goods and articles that have been cured by use of the said beneficial and relatively inexpensive accelerator system. The working proportional details and other significant specifics of the invention are also set forth in the following.

PARTICULARIZED DESCRIPTION OF THE INVENTION

The compounds or compositions of the present invention are, structurally, generically represented by the above-given Formula (I).

A good general procedure for preparation of the subject compounds is to charge a suitable inert (such as glass) reactor with an inert, anhydrous solvent and an alkali metal salt of O,O'-dialkylphosphorodithioic acid. The reactor is usually best purged with nitrogen to insure an anhydrous reaction medium. A solution of thiophosphoryl chloride in the same solvent is added; with the mixture subsequently refluxed to effect the desired reaction. The reaction mixture is then cooled; and a solution of an amine in the same solvent added; after which the reaction mixture is again refluxed to effect the desired reaction.

Unless attempts are made to isolate intermediate compounds; the finally-recovered products likely and usually contain minor amounts of variously substituted materials.

The desired reaction procedure may be generally typified by the following equations (in which the values of R, R', and R'' are as above stipulated):

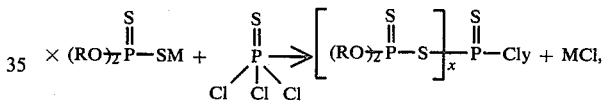

wherein "M" is an alkali metal (such as potassium) cation; and

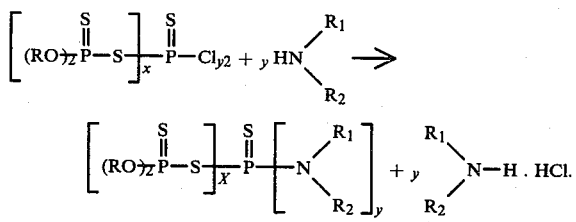

It is frequently found necessary that the crude product needs to be treated with a solvent in which KCl or equivalent alkali metal chloride and the amine hydrochloride salts are insoluble in order to permit effective removal of the salts by filtration or the like.

The products are then usually analyzed for carbon (C), nitrogen (N), phosphorus (P), and sulfur (S) as well as by infrared and the proton nuclear magnetic resonance (i.e., 'Hnmr) technique to confirm the actual composition of the involved products were actually obtained. Correlation of the infrared absorbances is in accordance with the procedures set forth in "Interpretation of the Infrared Spectra of Organophosphorus Compounds" by L. C. Thomas; Heyden & Son Ltd., 1974; as well as in other authoritative reference sources.

The Compounds of Formula (I), which, inter alia, are useful as accelerators, are ultimate derivatives of phosphorotetrathioic acid, which is of the structure:

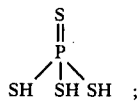

(A)

as well as, in certain instances (as in hereinafter abundantly clear of), phosphorodiamidodithioic acid, of the structure:

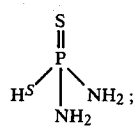

(B)

from which the grouping (or moiety), $(RO_2)P=S$, is referred to as the "O,O'-dialkylthiophosphoryl" group.

Accordingly, compounds of generalized Formula (I) are appropriately given the nomenclature: S,S'-di(O,O'-dihydrocarbylthiophosphoryl)-N-(hydrocarbyl)-phosphoramidotrithioate(s).

The more specific materials of the structure:

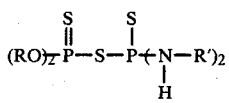

are likewise, appropriately named S-(O,O'-dihydrocarbylthiophosphoryl)-N,N'-di(hydrocarbyl)phosphorodiamidodithioates.

Particularly advantageous species of the compounds of the Formulae (I) and (IA) for utilization in practice of the present invention (with, for convenience, each particularly exemplified species also structurally formulated and codified and hereinafter referred to by the associated "R-No."), are as below-given:

| "R-No." | Formula For And Nomenclature Of Species Compound |
|---|---|
| "R-1" | $[(iso\text{-}C_3H_7O)_2P(S)\text{-}S\text{-}]_2\text{-}P(S)\text{-}N(H)\text{-}C_6H_5$, (I-1) which is S,S'-di-(O,O'-di-isopropylthiophosphoryl)-N-phenyl-phosphoramidotrithioate; |
| "R-2" | $(iso\text{-}C_3H_7O)_2P(S)\text{-}S\text{-}P(S)(\text{-}N(H)C_6H_5)_2$, (I-2) which is S-(O,O-diisopropylthiophosphoryl)-N,N'-(diphenyl)-phosphorodiamidodithioate; |
| "R-3" | $[(n\text{-}C_6H_{11}O)_2P(S)\text{-}S\text{-}]_2\text{-}P(S)\text{-}N(\text{-}C_3H_7\text{-}n)_2$, (I-3) which is S,S'-di-(O,O'-di-n-hexylthiophosphoryl)-N-(di-n-propyl)-phosphoroamidotrithioate; and |
| "R-4" | $(n\text{-}C_6H_{13}O)_2P(S)\text{-}S\text{-}P(S)(\text{-}N(\text{-}C_3H_7\text{-}n)_2)_2$, (I-4) which is S-(O,O'-di-n-hexylthiophosphoryl)-N,N'-(tetra-n-propyl)-phosphorodiamidodithioate. |

Also in keeping with one aspect of practice of the present invention, the compounds of Formula (I) and (IA) find excellent usage as curing agents or accelerators for the vulcanization of natural or synthetic rubber when they are employed in novel compositions, in effective minor proportion with respect to the mass of rubber being cured.

For such purposes of utilization and as is readily comprehended by those skilled in the art, the optimum particular respective proportions and measures to utilize for curing any given rubber system to be vulcanized depends in great measure on the specific utilized compounds (or mixtures thereof) of the Formula (I)—including possible mixtures therewith of either suitable accelerator and the like compounds—that are utilized and the specific rubber stock being compounded and vulcanized. In any event, the most satisfactory and effective amounts of the accelerator additive compound to incorporate for compounding in the rubber mass or stock to be vulcanized can be readily determined by simple and straightforward testing for any given embodiments desired to be utilized.

Nonetheless, it is frequently advantageous to observe the following recipe parameters insofar as actual accelerator content is concerned, with all numerically indicated concentration values being based and only approximately quantified on either parts by weight of the curing agent component per hundred parts by weight of rubber mass in the admixed and compounded vulcanizable stock (i.e., "phr") or on total charged moles of combined accelerator taken as molar concentration in gram (or other weight parts) moles per hundred (100) grams (or other weight units) of rubber. Along this line, molar concentration is literally generally a more directly recognizable indication of accelerator effectiveness which is directly dependent on the functional capability of the quantity of the additive concentrated in the mass.

| Accelerator Concentration | Broad, Generally Functional Range | Sometimes Preferred Range |
|---|---|---|
| In phr | 0.25–10.0 | 1.5–5.5 |
| Molar | 0.0025–0.020 | 0.005–0.010 |

Oftentimes, less of any particular given lower molecular weight species of the accelerator components possible to employ is required in comparison to the gravimetric requirements involved when higher molecular weight materials are utilized.

The accelerator additive composition of the present invention is handled, mixed into by compounding and treated or processed for curing and vulcanization of the rubber stock in standard and well known ways following conventional means and procedures for the operation. Of course, other conventional ingredients, including especially sulfur or the like or equivalent, all as desired and/or required in and for any given instance.

The rubber to be cured and vulcanized by practice of the present invention for making the cured rubber product for use in tire manufacture and for other rubber product purposes may be natural rubber (otherwise known as Hevea Brasiliensis) or conjugated diolefine polymer synthetic rubber or mixtures of any of them including their reclaims used at least partially for the stock being worked.

Such conjugated diolefine polymer synthetic rubbers are polymers of butadienes-1,3, e.g., butadiene-1,3, isoprene, 2,3-dimethylbutadiene-1,3, and copolymers of mixtures thereof, and copolymers of mixtures of one or more such butadienes-1,3, for example, up to 75 percent by weight of such mixture of one or more monoethylenic compounds which contain a

group, wherein at least one of the disconnected valences is attached to an electronegative group, that is, a group which substantially increases the electrical dissymmetry or polar character of the molecule.

Examples of compounds which contain a

group and are copolymerizable with butadienes-1,3 are: aryl olefines, such as styrene, vinyl toluene, alphamethylstyrene, chlorostyrene, dichlorostyrene, vinyl naphthalene; the unsaturated carboxylic acids and their esters, nitriles and amides, such as acrylic acid, methyl acrylate, ethyl acrylate, methyl methacrylate, acrylonitrile, methacrylonitrile, methacrylamide, vinylpyridines, such as 2-vinylpyridine, 2-methyl-5-vinylpyridine; methyl vinyl ketone, and methyl isopropenyl ketone.

Examples of such conjugated diolefine polymer synthetic rubbers are polybutadiene, polyisoprene, butadiene/styrene copolymers (i.e., "SBR") and butadiene/acrylonitrile copolymers. The synthetic rubber may be solution-prepared or emulsion-prepared, be it a stereospecific variety or otherwise.

Other conventional unsaturated sulfur-vulcanizable rubbers may be used, such as "EPDM" (rubbery terpolymer of ethylene, propylene and a copolymerizable non-conjugated diene such as 1,4-hexadiene, dicyclopentadiene, dicyclooctadiene, methylenenenorbornene, ethylidenenorbornene, tetrahydroindene, etc.). The analogous fluorocarbon, silicone and polysulfide rubbers may also be employed.

The rubber stock to be compounded and vulcanized, as has been mentioned, can also and as is needed contain conventional compounding and vulcanizing ingredients such as carbon black, rubber processing or softening oils (which may be added as such or as may be present from oil-extended rubbers), antioxidants, sulfur, zinc oxide and so forth.

EXEMPLIFICATIONS OF THE INVENTION

The following procedures, as set forth and explained in the below-given First through Fourth Examples, were employed for preparation and identification of Compounds "R-1" through "R-4", respectively and inclusive, in accordance with the present invention;

FIRST EXAMPLE (Preparation of Compound "R-1" of the Formula (I-1), above-given)

A one liter three-neck glass flask was fitted with: a nitrogen gas purge; a pot thermometer; condenser, dropping funnel; magnetic stirrer and heating mantel. This entire assembly was used as the reaction flask. Dry tetrahydrofuran (300 cc) and 25.24 grams (0.10 mole) of potassium O,O'-diisopropylphosphorodithioate were charged and a solution of 8.47 grams (0.05 mole) of thiophosphoryl chloride in 200 cc of tetrahydrofuran added. The mixture was then refluxed for approximately 13 hours, cooled and a solution of 9.31 grams (0.10 mole) of aniline in 200 cc tetrahydrofuran added. The mixture was then refluxed for about 6.5 hours, cooled and filtered to remove insoluble salts (KCl and aniline hydrochloride). Tetrahydrofuran was stripped from the filtrate and about one liter of diethyl ether added to the crude product. The resulting mixture was filtered to remove additional salt and the filtrate stripped of ether to give in high yield, a light-yellow oleaginous product.

Analyses for carbon, nitrogen, phosphorus and sulfur were 39.3%, 1.8%, 12.0%, and 21.7%, respectively.

Theory for $C_{18}H_{34}NO_4P_3S_5$ requires 37.16% C, 2.41% N, 15.98% P and 27.65% S. These analytical data indicate that the final product was not analytically pure and probably contained some diamidate of the structure of Formula (I-2).

Nonetheless, the infrared spectrum of the product was in general accord with the disclosed structure of the Formula (I-1). The spectrum contained an aromatic absorbance at approximately 3050 cm$^{-1}$; a sharp doublet of approximately equal intensity at about 1385 cm$^{-1}$ (which was correlated with the isopropyl group). A sharp single absorbance at 1600 cm$^{-1}$ was correlated with the "N-H" grouping/a broad absorbance centered at about 995 cm$^{-1}$ was correlated with the "P-O-aliphatic" grouping and an absorbance at approximately 975 cm$^{-1}$. This was correlated with the "P-NH aromatic" grouping. A sharp absorbance at 660 cm$^{-1}$ was correlated with the "P=S" function.

The 'Hnmr spectrum of the product was also in general agreement with the disclosed structure. The methyl protons of the isopropyl groups appeared as a doublet of about equal intensity at 1.38 ppm; and the methine proton appeared as a heptet centered at 4.88 ppm. The aromatic protons appeared as a multiplet centered at about 7.3 ppm.

SECOND EXAMPLE (Preparation of Compound "R-2" of the Formula (I-2), above-given)

A one liter three-neck glass flask was used as the reaction vessel. Dry tetrahydrofuran (300 cc) along with 25.24 grams (0.10 mole) of potassium O,O'-diisopropylphosphorodithioate was charged to the flask and a solution of 16.94 grams (0.10 mole) of thiophosphoryl chloride in 200 cc tetrahydrofuran were added. The mixture was then refluxed for approximately 9 hours and cooled. A solution of 37.25 grams (0.40 mole) of aniline in 200 cc tetrahydrofuran were then added. The mixture was then refluxed for 3 hours, cooled and filtered to remove salts (KCl and aniline hydrochloride). Tetrahydrofuran was stripped and the residue (an oil with suspended solids) was diluted with 100 cc of diethyl ether and filtered to remove additional salts. This procedure was repeated using 900 cc of ether. The final product was a lightyellow oil.

The actual yield was almost quantitative.

Analyses for carbon, nitrogen, phosphorus and sulfur were 48.5%, 5.2%, 9.8% and 19.5%, respectively. Theory for $C_{18}H_{26}N_2O_2P_2S_3$ requires 46.94% C, 6.08% N, 13.45% P and 20.89% S. These results indicate that the final product was not analytically pure and probably contained some monoamidate of the structure of Formula (I-1).

The infrared spectrum of the product was in general accord with the disclosed structure of the Formula (I-2). The spectrum contained an aromatic absorbance at about 3050 cm$^{-1}$; a sharp single absorbance at 1600 cm$^{-1}$ correlated with the "N-H" grouping; a broad absorbance centered at about 995 cm$^{-1}$ which was correlated with the "P-O-aliphatic" group; a medium absorbance at about 975 cm$^{-1}$ which was correlated with the "P-NH aromatic" grouping; and a relatively sharp absorbance at 675 cm$^{-1}$ which was correlated with the "P=S" function.

The 'Hnmr spectrum of the product was in general accord with the disclosed structure of Formula (I-2). It was observed that the "N-H" proton was deschielded, presumably by the phosphorus atom, relative to a reference spectrum on aniline.

THIRD EXAMPLE (Preparation of Compound "R-3" of the Formula (I-3), above-given)

To a one (1) liter glass flask there were charged: 300 cc of benzene; and 67.3 grams (0.20 mole) of potassium O,O'-di-n-hexylphosphorodithioate.

A solution of 16.9 grams (0.10 mole) of thiophosphoryl chloride in 200 cc of benzene was added to the reaction flask. The mixture was then refluxed for approximately 12.5 hours. The mixture was then cooled. After that a solution of 20.2 grams di-n-propylamine (0.20 mole) in 200 cc of benzene were added. A moderate exotherm was noted.

The mixture was then refluxed for about 7 hours, cooled and filtered to remove insoluble salts (KCl and amine hydrochloride).

Benzene was then evaporated from the filtrate to give a crude product which was a turbid, light-yellow oil. The crude product was then mixed with 500 cc diethyl ether and filtered to remove additional salt. This ether treatment was repeated to ensure removal of all the salt from the desired product. After stripping ether and vacuum drying, a total of 75.4 grams (proportioned to a 99.5% yield) of a light yellow liquid was isolated. This product was treated with one gram of $K_2CO_3$ in ether solution. It was then filtered and the ether stripped to remove a trace amount of free acid.

About 37.4 grams (or only 49.3% yield) of light-yellow oil recovery was used for further analysis and testing.

Analyses for carbon, nitrogen, phosphorus and sulfur were 48.0%, 2.2%, 9.2%, and 18.4%, respectively. Theory for $C_{30}H_{66}NO_4P_3S_5$ is 47.53% C, 1.85% N, 12.26% P, and 21.15% S. These analyses indicate that the final product contained some diamidate of the structure of Formula (I-4) above-given).

The infrared spectrum of the resultant product contained: a broad absorption at 995 cm$^{-1}$; a broad peak at about 950 cm$^{-1}$; and a relatively sharp peak at 675 cm$^{-1}$. These respective absorption peaks were correlatable to the "P—O—CH$_2$R", "P—N—R$_2$" and "P=S" groups.

The 'Hnmr of the isolated product was also in accord with the disclosed structure of the Formula (I-3). The spectrum contained a multiplet centered at about 3.1 ppm. It was also accordingly correlatable with the methylene groups adjacent to the nitrogen atom. In contrast, the triplet of the methylene groups adjacent to the nitrogen atom in di-n-propylamine was observed at 2.63 ppm.

FOURTH EXAMPLE (Preparation of Compound "R-4" of the Formula (I-4), above-given)

To a one liter three-neck flask was charged: 200 cc of dry tetrahydrofuran; and 16.8 grams (0.05 mole) of potassium O,O'-di-n-hexylphosphorodithioate.

A solution of 8.5 grams (0.05 mole) of thiophosphoryl chloride in 100 cc of dry tetrahydrofuran was added over 10 minutes to the reaction flask. A slight exothermic reaction was noted. The reaction mixture was then refluxed for approximately 2 hours. It then was cooled to about 10° C. A solution of 20.24 grams (0.20 mole) of di-n-propylamine in 100 cc dry tetrahydrofuran was then added over a 15 minute period. The reaction, as it was observed, was noted to be slightly exothermic.

The reaction mixture was then heated and refluxed for about one hour, cooled and filtered to remove insoluble salts (KCl and amine hydrochloride). Tetrahydrofuran was stripped from the filtrate to give 46.4 grams of crude product which contained amine hydrochloride. The crude product was then successively slurried in benzene, chloroform and diethyl ether. After each treatment, the slurry was filtered to remove salt and the solvent stripped to recover product.

A total of 24.9 grams of light amber liquid were recovered; 88.8% yield. This product was then treated with one gram of $K_2CO_3$ in 100 cc of diethyl ether to remove any unreacted acid, filtered and ether removed to give the final product; a light amber liquid in essentially the same yield.

FIFTH EXAMPLE (Utility Test Results As Rubber Vulcanization Accelerators of Compounds According To The Invention)

To demonstrate the advantageous practice in use as rubber accelerators of the novel compositions of the present invention, a number of samples of a common and widely commercially employed oil-extended SBR stock were compounded and tested with the compounds above identified as "R-1" through "R-4", inclusively, for employment as accelerator additives in accordance with the present invention to determine their individual vulcanization rate characteristics. Each of the samples investigated was prepared according to a standard recipe or base compound formulation which was (with all parts therein taken by weight):

| Ingredient | Parts |
| --- | --- |
| Oil-Extended SBR | 145 (Containing 45 parts Mineral Oil) |
| Carbon Black | 70 |
| Stearic Acid | 2 |
| Zinc Oxide | 2 |
| Stabilizer (Antioxidant) | 1.0 |
| Sulfur | 1.7 |
| Total Accelerator | Variable (as shown) |

The method used to prove efficacy of the accelerator additive was to first determine an appropriate Cure Time to obtain optimum rates of vulcanization for each sample.

In this connection and as is comprehended by those skilled in the art, the Cure Time (or $T_c$) for any given sample is inolved in its Cure Rate Index (i.e., "CRI").

CRI is defined as:

$$\frac{1}{(T_c - T_s)} \times 100,$$

or the reciprocal of the difference between $T_c$ (which is the time necessary to achieve a 90 percent cure) and $T_s$ (time to scorch, that is, the time taken to achieve a tow-torque unit rise) multiplied by 100. A MONSANTO Rheometer is used in these literally standard tests; with specific conditions employed being: operation at 100 rpm; use of the minidie attachment in the apparatus; and the effecting of a one degree arc at 149° C. during the test procedure.

The reasons for use of the indicated test, as is well known, are plain and fundamentally sound. Rheometer data are based on torque measurements. These, including significant maximum torque measures, are indicative at any given point of measure of the state of cure of the vulcanizing sample. The time required to increase the torque is readily indicative of the particularly involved rate of the vulcanization reaction. The involved units of torque are generally expressed in Neuton meters, (Nm). The scorch and cure times are generally expressed in minutes.

The basic MONSANTO Rheometer data obtained with Compounds "R-1" through "R-4" inclusive, are related in the following TABLE I.

TABLE I

| MONSANTO RHEOMETER RESULTS | | | | |
|---|---|---|---|---|
| Base Compound Plus | Minutes to $T_s$II | Minutes to $T_c$ | Torque, Maximum (N m) | CRI |
| 3.4 phr "R-1" | 11.0 | 60.6 | 2.58 | 2.0 |
| 2.7 phr "R-2" | 10.6 | 63.3 | 2.54 | 1.9 |
| 4.5 phr "R-3" | 3.4 | 16.0 | 3.20 | 7.9 |
| 3.3 phr "R-4" | 5.3 | 19.3 | 3.29 | 4.1 |

The tabulated data plainly indicate that the novel compositions of the present invention, when employed as accelerators also by way of practice pursuant to the present invention, impart good scorch resistant properties as well as reasonably attractive cure rates to the compounded rubber stock materials in which they are incorporated.

After Cure Time (i.e., practical $T_c$) determination, each given sample composition was vulcanized over suitable time ranges. The vulcanized sample specimens were then tested by standard and well known procedures for their obtained values of: (i) 300% Modulus; (ii) Tensile Strength; and (iii) percentage Elongation in order to find and fix the conventionally sought Stress/Strain data applicable to each.

These data, insofar as force measurements were and are involved, were actually taken (with the appropriate test apparatus commonly employed for the purpose) in the English System of pounds-force/inch$^2$ (i.e., "psi"). For convenience, the Metric System equivalents in megapascals (i.e., "MPa") are also reproduced with the hereinincluded data. In this, MPa values are simply and straightforwardly obtained upon multiplication of any psi value by the numerical conversion factor 0.006894757. Generally, to accommodate involved practicalities of the testing precision, to so-converted psi values are rounded off to the nearest unit of tenths, 0.1, in MPa values as, for example, giving a value of 6.9 MPa for the equivalent of 1,000 psi since the actually calculable numerical equivalent obtainable using the given multiplication factor is 6.894757.

The specific testing results obtained with Compounds "R-1" through "R-4", inclusive, are set forth in the following second tabulation.

TABLE II

| CURE TEST RESULTS | | | | | | | |
|---|---|---|---|---|---|---|---|
| Compound No. | phr | Cure Time Minutes | 300% Modulus psi | 300% Modulus MPa | Tensile Strength psi | Tensile Strength MPa | Percent (%) Elongation |
| "R-1" | 3.4 | 15 | 200 | 1.4 | 590 | 4.1 | 930 |
|  |  | 23 | 300 | 2.1 | 1300 | 9.0 | 870 |
|  |  | 30 | 340 | 2.3 | 1650 | 11.4 | 870 |
| "R-2" | 2.7 | 15 | 120 | 0.8 | 250 | 1.7 | 1000 |
|  |  | 23 | 195 | 1.3 | 660 | 4.6 | 950 |
|  |  | 30 | 240 | 1.7 | 1000 | 6.9 | 875 |
| "R-3" | 4.5 | 15 | 900 | 6.2 | 2995 | 20.6 | 670 |
|  |  | 23 | 1020 | 7.0 | 2900 | 20.0 | 600 |
|  |  | 30 | 1040 | 7.2 | 2920 | 20.1 | 600 |
| "R-4" | 3.3 | 15 | 780 | 5.4 | 2580 | 17.8 | 660 |
|  |  | 23 | 980 | 6.8 | 3000 | 20.7 | 640 |
|  |  | 30 | 1035 | 7.1 | 2950 | 20.3 | 615 |

All of these delineated results, by the way, compare favorably with those obtainable using standard accelerator additives for rubber(s). This includes such of those as the common modern day material known and obtainable as "Santocure NS" (commercially available under the indicated trade-designation from MONSANTO COMPANY of St. Louis, Mo. and which is N-tert.-butylbenzothiazolesulfenamide). Obviously, this is an exceptionally attractive and commendable feature and incentive for practice of the present invention giving fair regard and consideration to the relative economies involved and achievable with use of the presently contemplated accelerator additives.

Similar good results are obtainable with the same and other vulcanizable natural and synthetic rubbers using different species and concentrations for accelerator materials possible to employ within the scope of the invention using the novel compounds according to the above Formulae (I) and (IA).

Likewise and surprisingly enough, good and satisfactory results are obtainable when the compounds of Formula (I) and Formula (IA) are utilized in standard ways and in conventional formulations and compounding recipes for use as insecticides and as additives for mineral lubricating oil preparations.

Many changes and modifications can readily be made and adapted in embodiments in accordance with the present invention without substantially departing from its apparent and intended spirit and scope, all in pursuance and accordance with same as it is set forth and defined in the hereto appended claims.

We claim:

1. As a composition of matter, an S,S',di-(O,O'-dihydrocarbylthiophosphoryl)-N(hydrocarbyl)phosphoroamidotrithioate of the general structure and Formula:

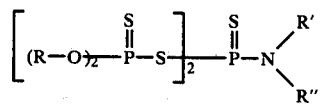

wherein R, R' and R" are independently selected from the group consisting of methyl, ethyl, n-propyl, isopropyl, n-butyl, n-butyl isomers, cyclohexyl, octyl, octyl isomers, stearyl and phenyl.

2. As a composition matter, an S-(O,O'-dihydrocarbylthiophosphoryl)-N,N'-di-(hydrocarbyl)phosphorodiamidodithioate of the general structure and Formula:

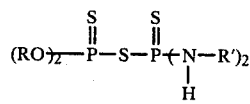

wherein R and R' are independently selected from the group consisting of methyl, ethyl, n-propyl, isopropyl, n-butyl, n-butyl isomers, cyclohexyl, octyl, octyl isomers, stearyl and phenyl.

3. As a composition of matter, S,S'-di(O,O'-di-isopropylthiophosphoryl)-N-phenyl-phosphoramidotrithioate.

4. As a composition of matter, S-(O,O-diisopropylthiophosphoryl)-N,N'-(diphenyl)phosphorodiamidodithioate.

5. As a composition of matter S,S'-di(O,O'-di-n-hexylthiophosphoryl)-N-(di-n-propyl)-phosphoramidotrithioate.

6. As a composition of matter, S-(O,O'-di-n-hexylthiophosphoryl)-N,N'-(tetra-n-propyl)-phosphorodiamidodithioate.

* * * * *